(12) United States Patent
Masuda et al.

(10) Patent No.: US 9,968,591 B2
(45) Date of Patent: May 15, 2018

(54) ANTIFUNGAL COMPOSITION

(71) Applicants: Pola Pharma Inc., Tokyo (JP); Nihon Nohyaku Co., Ltd., Tokyo (JP)

(72) Inventors: Takaaki Masuda, Yokohama (JP); Naoto Nishida, Yokohama (JP); Naoko Kobayashi, Yokohama (JP); Hideaki Sasagawa, Yokohama (JP)

(73) Assignees: Pola Pharma Inc., Tokyo (JP); Nihon Nohyaku CO., LTD., Tokyo (JP)

( * ) Notice: Subject to any disclaimer, the term of this patent is extended or adjusted under 35 U.S.C. 154(b) by 142 days.

(21) Appl. No.: 14/539,530

(22) Filed: Nov. 12, 2014

(65) Prior Publication Data

US 2015/0073028 A1    Mar. 12, 2015

Related U.S. Application Data

(62) Division of application No. 12/676,345, filed as application No. PCT/JP2008/066057 on Sep. 5, 2008, now abandoned.

(30) Foreign Application Priority Data

Sep. 5, 2007   (JP) .................................. 2007-229618

(51) Int. Cl.
| | | |
|---|---|---|
| *A61K 31/4178* | (2006.01) | |
| *A61K 9/00* | (2006.01) | |
| *A61K 47/10* | (2017.01) | |
| *A61K 47/12* | (2006.01) | |
| *A61K 47/14* | (2017.01) | |
| *A61K 47/26* | (2006.01) | |
| *A61K 47/32* | (2006.01) | |
| *A61K 47/34* | (2017.01) | |
| *A61K 47/22* | (2006.01) | |

(52) U.S. Cl.
CPC ........ *A61K 31/4178* (2013.01); *A61K 9/0014* (2013.01); *A61K 47/10* (2013.01); *A61K 47/12* (2013.01); *A61K 47/14* (2013.01); *A61K 47/22* (2013.01); *A61K 47/26* (2013.01); *A61K 47/32* (2013.01); *A61K 47/34* (2013.01)

(58) Field of Classification Search
CPC .... A61K 31/4178; A61K 47/10; A61K 47/12; A61K 47/14; A61K 47/22; A61K 47/26; A61K 47/32; A61K 47/34; A61K 9/0014
See application file for complete search history.

(56) References Cited

U.S. PATENT DOCUMENTS

| | | | |
|---|---|---|---|
| 4,267,169 A | 5/1981 | Kamishita et al. | |
| 4,636,520 A | 1/1987 | Umio et al. | |
| 4,764,381 A | 8/1988 | Bodor et al. | |
| 5,061,700 A * | 10/1991 | Dow .................... | A61K 9/0014 514/169 |
| 5,340,836 A | 8/1994 | Reinhard et al. | |
| 5,690,923 A | 11/1997 | De Vringer et al. | |
| 5,753,256 A | 5/1998 | Cordes et al. | |
| 5,814,305 A | 9/1998 | Laugier et al. | |
| 5,962,536 A | 10/1999 | Komer | |
| 5,993,787 A | 11/1999 | Sun et al. | |
| 6,007,791 A | 12/1999 | Coombes et al. | |
| 6,008,256 A | 12/1999 | Haraguchi et al. | |
| 6,017,920 A | 1/2000 | Kamishita et al. | |
| 6,083,518 A | 7/2000 | Lindahl | |
| 6,428,654 B1 | 8/2002 | Cronan, Jr. et al. | |
| 6,541,517 B1 * | 4/2003 | Murphy ............... | A61K 31/225 514/547 |
| 6,585,963 B1 | 7/2003 | Quan et al. | |

(Continued)

FOREIGN PATENT DOCUMENTS

| | | |
|---|---|---|
| EP | 0070525 | 1/1983 |
| EP | 0440298 | 8/1991 |

(Continued)

OTHER PUBLICATIONS

Gupta et al. 2004. Am. J. Clin. Dermatol., 5(6), pp. 417-422.*

(Continued)

*Primary Examiner* — Kara R McMillian
(74) *Attorney, Agent, or Firm* — Knobbe, Martens, Olson & Bear, LLP

(57) ABSTRACT

Disclosed is a pharmaceutical composition for antifungal use, comprising: 1) one or more compounds selected from compounds represented by the general formula (1) below and physiologically acceptable salts thereof; 2) one or more compounds selected from polypropylene glycol, diesters of dibasic acids, triacetin, 2-ethyl-1,3-hexanediol, lauromacrogol, and polyoxyethylene-polyoxypropylene glycol; and 3) one or more compounds selected from glucono-δ-lactone, propylene glycol, glycerin, and lactic acid. General formula (1) (In the formula, X represents a halogen or hydrogen).

General formula (1)

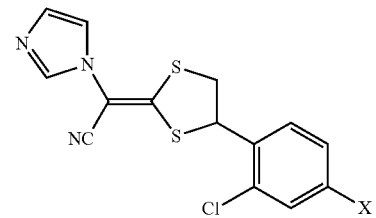

wherein X represents a halogen or hydrogen.

6 Claims, No Drawings

(56) References Cited

U.S. PATENT DOCUMENTS

| | | | |
|---|---|---|---|
| 6,740,326 | B1 | 5/2004 | Meyer et al. |
| 8,268,876 | B2 | 9/2012 | Miki et al. |
| 8,513,296 | B2 | 8/2013 | Masuda et al. |
| 2003/0017207 | A1 | 1/2003 | Lin et al. |
| 2003/0235541 | A1 | 12/2003 | Maibach et al. |
| 2004/0208906 | A1 | 10/2004 | Tatara et al. |
| 2005/0232879 | A1 | 10/2005 | Sasagawa et al. |
| 2006/0140984 | A1 | 6/2006 | Tamarkin et al. |
| 2007/0099932 | A1 | 5/2007 | Shirouzu et al. |
| 2008/0031835 | A1 | 2/2008 | Kawamura et al. |
| 2009/0076109 | A1 | 3/2009 | Miki et al. |
| 2009/0099202 | A1 | 4/2009 | Shirouzu et al. |
| 2009/0137651 | A1 | 5/2009 | Kobayashi et al. |
| 2009/0202602 | A1 | 8/2009 | Ishima et al. |
| 2010/0168200 | A1 | 7/2010 | Masuda et al. |
| 2010/0173965 | A1 | 7/2010 | Masuda et al. |
| 2010/0204293 | A1 | 8/2010 | Masuda et al. |
| 2010/0210702 | A1 | 8/2010 | Vontz et al. |
| 2010/0210703 | A1 | 8/2010 | Vontz et al. |
| 2010/0249202 | A1 | 9/2010 | Koga et al. |

FOREIGN PATENT DOCUMENTS

| | | | |
|---|---|---|---|
| EP | 0715856 | A1 | 6/1996 |
| EP | 1138314 | | 10/2001 |
| EP | 1522316 | | 4/2005 |
| EP | 1537868 | | 6/2005 |
| EP | 1637132 | | 3/2006 |
| EP | 2005958 | A1 | 12/2008 |
| EP | 2005959 | | 12/2008 |
| EP | 2025337 | | 2/2009 |
| EP | 2191827 | | 6/2010 |
| EP | 1537868 | | 8/2011 |
| JP | 61-118315 | | 6/1986 |
| JP | 62-093227 | | 4/1987 |
| JP | 62-223163 | | 10/1987 |
| JP | 01-242525 | | 9/1989 |
| JP | 01-246219 | | 10/1989 |
| JP | 02-264723 | | 10/1990 |
| JP | 02-275877 | | 11/1990 |
| JP | 05-306223 | | 11/1993 |
| JP | 06-199701 | | 7/1994 |
| JP | 06-211651 | | 8/1994 |
| JP | 07-188027 | | 7/1995 |
| JP | 07-74144 | | 8/1995 |
| JP | 07-206711 | | 8/1995 |
| JP | 07-223971 | | 8/1995 |
| JP | 08-020527 | | 1/1996 |
| JP | 10-152433 | | 6/1998 |
| JP | 10-226639 | | 8/1998 |
| JP | 10-226686 | | 8/1998 |
| JP | 2001-064206 | | 3/2001 |
| JP | 2002-114680 | A | 4/2002 |
| JP | 2002-193755 | | 7/2002 |
| JP | 2002-284702 | | 10/2002 |
| JP | 2002-363070 | | 12/2002 |
| JP | 2003-252798 | | 9/2003 |
| JP | 2004-529923 | | 9/2004 |
| JP | 2005-104924 | A | 4/2005 |
| JP | 2005-154306 | | 6/2005 |
| JP | 2005-239678 | | 9/2005 |
| JP | 2005-289879 | | 10/2005 |
| JP | 2006-028123 | | 2/2006 |
| JP | 2006-306734 | | 11/2006 |
| RU | 2 270 894 | C2 | 3/2004 |
| WO | WO 90/14094 | | 11/1990 |
| WO | WO 95/30440 | | 11/1995 |
| WO | WO 96/11572 | * | 4/1996 |
| WO | WO 96/11710 | | 4/1996 |
| WO | WO 96/40047 | | 12/1996 |
| WO | WO 97/02821 | A2 | 1/1997 |
| WO | WO 97/07794 | | 3/1997 |
| WO | WO 00/01384 | | 1/2000 |
| WO | WO 02/062336 | | 8/2002 |
| WO | WO 02/083084 | | 10/2002 |
| WO | WO 02/087570 | | 11/2002 |
| WO | WO 03/020248 | | 3/2003 |
| WO | WO 03/105841 | | 12/2003 |
| WO | WO 2004/021968 | | 3/2004 |
| WO | WO 2004/084826 | | 10/2004 |
| WO | WO 2004/091521 | | 10/2004 |
| WO | WO 2005/099764 | | 10/2005 |
| WO | WO 2005/123136 | | 12/2005 |
| WO | WO 2006/038317 | | 4/2006 |
| WO | WO 2007/102241 | A1 | 9/2007 |
| WO | WO 2007/102242 | A1 | 9/2007 |
| WO | WO 2007/077806 | | 12/2007 |
| WO | WO 2008/075207 | | 6/2008 |
| WO | WO 2009/028495 | | 3/2009 |
| WO | WO 2010/093992 | A1 | 8/2010 |

OTHER PUBLICATIONS

Absolute ethanol MSDS (www.sciencelab.com/msds.php?msdsld=9923955) 7 pages (2011).

Article, "Treatment" in 2 pages downloaded from http://www.babymd,net/dryskin.htm date unknown.

Borrás-Blasco, et al. "A Mathematical Approach to Predicting the Percutaneous Absorption Enhancing Effect of Sodium Lauryl Sulphate," International Journal of Pharmaceutics, vol. 269, pp. 121-129, 2004.

Crotamiton Properties (http://www.chemspider.com/Chemical-Structure.2780.html) (downloaded Dec. 6, 2011).

Ethyl Cellulose Density downloaded from www.chemicalbook.com/ProductMSDSDetailCB6165620_EN.htm, 3 pages, copyright 2008.

Examination Report dated Apr. 8, 2010 to corresponding New Zealand Patent Application No. 571818.

GHS Classification Guidance for Enterprises (2nd Edition, Ministry of Economy, Trade and Industry, Japan, Mar. 2010) (downloaded Dec. 6, 2011).

Hoepfner et al., "Fiedler Lexikon der Hilfsstoffe für Pharmazie, Kosmetik und angrenzende Gebiete," ECV Editio Cantor Verlag Aulendorf, pp. [illegible], 1392-1393.

International Search Report dated Nov. 18, 2008 issued to international application No. PCT/JP2008/066056.

International Search Report dated Nov. 18, 2008 issued to international application No. PCT/JP2008/066057.

International Search Report dated Nov. 18, 2008 issued to international application No. PCT/JP2008/066058.

Martins, et al. "In vitro Sensitivity of Dermatophytes to Urea," Clinics, vol. 61, No. 1, pp. 9-14, 2006.

Methyl Ethyl Ketone MSDS (www.sciencelab.com/msds.php?msdsld=9927358) 6 pages (2011).

Niwano et al., "Efficacy of NND-502, a novel imidazole antimycotic agent, in experimental models of Candida albicans and Aspergillus fumigatus infections," International Journal of Antimicrobial Agents, vol. 12, pp. 221-228 (1999).

Niwano, et al. "In vitro and In vivo Antidermatophyte Activities of NND-4502, a Novel Optically Active Imidazole Antimycotic Agent," Antimicrobial Agents and Chemotherapy, vol. 42, No. 4, pp. 967-970, Apr. 1998.

Niwano, et al. "Lanoconazole and Its Related Optically Active Compound NND-502: Novel Antifungal Imidazoles with a Ketene Dithioacetal Structure," Current Medicinal Chemistry, vol. 2, pp. 147-160, 2003.

Office Action issued in European Patent Application No. 08829061.4, dated Apr. 19, 2013, corresponding to related U.S. Appl. No. 13/603,220.

Office Action issued in Japanese Patent Application No. 2009-531290 dated Apr. 23, 2013, corresponding to related U.S. Appl. No. 13/603,220.

Office action issued to related Israeli Patent Application No. 193894 dated Oct. 14, 2010 with translation.

Pluronics Density downloaded from www.chemicalbook.com/ChemicalProductPropertyEN_Cb2709101.htm, 2 pages, copyright 2010.

(56) References Cited

OTHER PUBLICATIONS

SDS Density downloaded from www.chemicalbook.com/ChemicalProductProperty_EN_CB2147453.htm, 2 pages, copyright 2010.
Supplemental European Search Report dated Aug. 10, 2010, issued to European patent application 06811053.5.
Supplementary European Search Report dated Aug. 12, 2010 issued to European patent application No. 08829224.8.
Supplementary European Search Report dated Aug. 12, 2010 to European application No. 08829061.4.
Supplementary European Search Report dated Aug. 16, 2010 and issued to European application No. 06811056.8-2123/2005958.
Uchida, et al. "In vitro Activity of Novel Imidazole Antifungal Agent NND-502 Against *Malassezia* Species," International Journal of Antimicrobial Agents, vol. 21, pp. 234-238, 2003.
Uchida et al, "In vitro antifungal activity of luliconazole (NND-502), a novel imidazole antifungal agent," Journal of Infection and Chemotherapy, vol. 10(4), pp. 216-219 (2004).
Vieira, et al. "Cationic Lipids and Surfactants as Antifungal Agents: Mode of Action," Journal of Antimicrobial Chemotherapy, Vo. 58, pp. 760-767, 2006.

* cited by examiner

ANTIFUNGAL COMPOSITION

TECHNICAL FIELD

The present invention relates to a pharmaceutical composition, and more specifically, to a pharmaceutical composition for antifungal use.

BACKGROUND ART

In Japan having a hot and humid climatic property, measures against mycoses caused by pathogenic fungi are a particularly important pharmaceutical theme. Reoccurrence of such a disease is repeatedly caused by remaining living microbes even if the disease appears to have been perfectly cured. For example, summer is a season in which the disease easily reoccurs, and thus, repetitive treatments are required. Therefore, an antifungal agent having an excellent medicinal effect has been demanded. Further, simultaneously, mycoses include those which develop on hand and foot portions such as tinea pedis and tinea unguium, those which develop on the body skin such as tinea, and those which develop on the scalp such as seborrheic dermatitis, and there is also a demand for development of a versatile dosage form which can be applied to the respective portions.

As an antifungal agent having an excellent antifungal effect, for example, luliconazole, one of compounds represented by the general formula (1), has attracted attention as a medicament that allows a treatment period to be shortened (for example, see JP 09-100279 A and JP 02-275877 A). Such compounds are also useful for onychomycosis, and a formulation thereof for onychomycosis, which is a hydrogel-like formulation, is also already known (for example, see WO 03/105841). Thus, the compounds represented by the general formula (1) can be said to be excellent in antifungal property as well. However, the compounds represented by the general formula (1) are poorly-soluble in an aqueous medium in terms of solubility, and must be formulated by using a solubilizing agent. As a result, the control of a variation in the bioavailability of medicaments to be caused by such a solubilizing agent has been the single and greatest problem in a formulation study. In particular, in the case of allowing a cellulose-based thickener or the like to coexist for viscosity adjustment, the addition of such a cellulose-based thickener also has an action of enhancing a horny cell layer storage (hereinafter, also referred to as a storage or a retention of a medicament in the horny cell layer). Thus, in some cases, a variation in the compounding amount of such a thickener for viscosity adjustment has also caused a change in the pharmacodynamic property and a change in the bioavailability of a formulation. A medicine is always required to retain bioequivalence, and it can be said that the development of a system capable of compensating such a change in the pharmacodynamic property and of maintaining bioequivalence has been demanded for the formulation design of the compounds represented by the general formula (1).

Meanwhile, there has not been known any pharmaceutical composition for antifungal use containing: 1) one or more compounds selected from compounds represented by the general formula (1) below and physiologically acceptable salts thereof; 2) one or more compounds selected from polypropylene glycol, diesters of dibasic acids, triacetin, 2-ethyl-1,3-hexanediol, lauromacrogol, and polyoxyethylene-polyoxypropylene glycol; and 3) one or more compounds selected from glucono-δ-lactone, propylene glycol, glycerin, and lactic acid. Further, there has been no finding that a change in the bioavailability of the compounds represented by the general formula (1) due to a variation in the formulation components can be compensated by adopting such a composition.

It should be noted that, there are already known techniques of incorporating ingredients such as polypropylene glycol, diesters of dibasic acids, triacetin, 2-ethyl-1,3-hexanediol, lauromacrogol, polyoxyethylene-polyoxypropylene glycol, glucono-δ-lactone, propylene glycol, glycerin, or lactic acid into a pharmaceutical composition for antifungal use for the purpose of serving as an absorption accelerant, a pH stabilizer, or the like (for example, see JP 2004-529935 A, JP 2003-252798 A, JP 2004-529923 A, WO 96/011710, and WO 01/003742).

General formula (1)

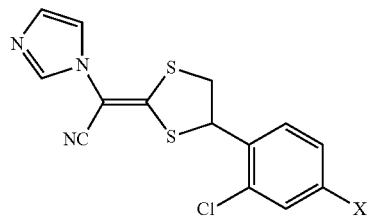

wherein X represents a halogen or hydrogen.

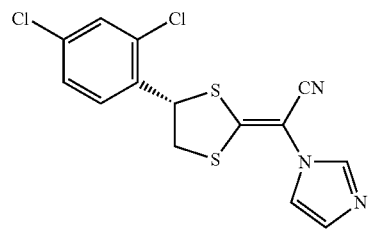 [SMILES: N#C/C(=C1/SC[C@H](c2ccc(Cl)cc2Cl)S1)n1ccnc1]

DISCLOSURE OF THE INVENTION

Technical Problem

The present invention has been made under such circumstances, and is characterized by providing a system for compensating a change in the bioavailability of compounds represented by the general formula (1) due to a variation in the formulation components.

In view of such circumstances, the inventors of the present invention have intensively studied to search a system for compensating a change in the bioavailability of the compounds represented by the general formula (1) due to a variation in the formulation components. As a result, the inventors have found that the horny cell layer storability of the compounds represented by the general formula (1) can be controlled by formulating a combination of a ingredient for inhibiting the absorption of the compounds of the general formula (1) to the horny cell layer, i.e., one or more compounds selected from polypropylene glycol, diesters of dibasic acid, triacetin, 2-ethyl-1,3-hexanediol, lauromacrogol, and polyoxyethylene-polyoxypropylene glycol, and a ingredient for promoting the absorption of the compounds of the general formula (1) to the horny cell layer, i.e., one or more compounds selected from glucono-δ-lactone, propylene glycol, glycerin, and lactic acid, and changing the combination of those two ingredients. Thus, the present invention has been completed. That is, the present invention is as follows.

<1> A pharmaceutical composition for antifungal use, comprising: 1) one or more compounds selected from compounds represented by the general formula (1) and physiologically acceptable salts thereof; 2) one or more compounds selected from polypropylene glycol, diesters of dibasic acids, triacetin, 2-ethyl-1,3-hexanediol, lauromacrogol, and polyoxyethylene-polyoxypropylene glycol; and 3) one or more compounds selected from glucono-δ-lactone, propylene glycol, glycerin, and lactic acid.

<2> The pharmaceutical composition according to the item <1>, wherein the compound represented by the general formula (1) is luliconazole.

<3> The pharmaceutical composition according to the item <1> or <2>, comprising triacetin as one or more compounds selected from polypropylene glycol, diesters of dibasic acids, triacetin, 2-ethyl-1,3-hexanediol, lauromacrogol, and polyoxyethylene-polyoxypropylene glycol.

<4> The pharmaceutical composition according to any one of the item <1> to <3>, comprising glucono-δ-lactone as one or more compounds selected from glucono-δ-lactone, propylene glycol, glycerin, and lactic acid.

<5> The pharmaceutical composition according to any one of the item <1> to <4>, wherein the pharmaceutical composition for antifungal use is in the form of a single-phase solution.

<6> The pharmaceutical composition according to any one of the item <1> to <5>, further comprising ethanol and/or water.

<7> The pharmaceutical composition according to any one of the item <1> to <6>, wherein the target disease is seborrheic dermatitis.

<8> A method for adjusting the storability in the horny cell layer of compounds represented by the general formula (1) and/or salts thereof in the pharmaceutical composition according to any one of the item <1> to <7>, which comprises decreasing the total content of one or more compounds selected from polypropylene glycol, diesters of dibasic acids, triacetin, 2-ethyl-1,3-hexanediol, lauromacrogol, and polyoxyethylene-polyoxypropylene glycol with respect to the total amount of the pharmaceutical composition, and/or increasing the total content of one or more compounds selected from glucono-δ-lactone, propylene glycol, glycerin, and lactic acid with respect to the total amount of the pharmaceutical composition, in the case where the storability in the horny cell layer should be increased; or increasing the total content of one or more compounds selected from polypropylene glycol, diesters of dibasic acids, triacetin, 2-ethyl-1,3-hexanediol, lauromacrogol, and polyoxyethylene-polyoxypropylene glycol with respect to the total amount of the pharmaceutical composition, and/or decreasing the total content of one or more compounds selected from glucono-δ-lactone, propylene glycol, glycerin, and lactic acid with respect to the total amount of the pharmaceutical composition, in the case where the storability in the horny cell layer should be decreased.

Effect of the Invention

According to the present invention, there may be provided a system for compensating a change in the bioavailability of compounds represented by the general formula (1) due to a variation in the formulation components.

BEST MODE FOR CARRYING OUT THE INVENTION

<1> Compounds Represented by General Formula (1) as Essential Ingredients in Pharmaceutical Composition of Present Invention The pharmaceutical composition of the present invention is one for antifungal use, and characterized by containing a compound represented by the general formula (1) and/or a salt thereof.

When X in the compounds represented by the general formula (1) represents a halogen, preferred examples of the halogen include chlorine, bromine, iodine, and fluorine. Of those, chlorine is particularly preferred.

In addition, preferred specific examples of the compounds represented by the general formula (1) include (R)-(−)-(E)-[4-(2,4-dichlorophenyl)-1,3-dithiolane-2-ylidene]-1-imidazolylacetonitrile (luliconazole), (R)-(+)-(E)-[4-(2-chlorophenyl)-1,3-dithiolane-2-ylidene]-1-imidazolylacetonitrile, and (E)-[4-(2-chlorophenyl)-1,3-dithiolane-2-ylidene]-1-imidazolyl acetonitrile (lanoconazole). Those compounds are known compounds and their production methods and antifungal properties have already been known (for example, see JP 62-93227 A). Of those, luliconazole is preferred because it ensures the effect of the present invention to be particularly large.

Further, the "physiologically acceptable salts thereof" as described above are not particularly limited as long as the salts are physiologically acceptable, and favorable examples of the salts include: mineral acid salts such as a hydrochloride, a nitrate, a sulfate, and a phosphate; organic acid salts such as a citrate, an oxalate, a lactate, and an acetate; and sulfate-containing salts such as a mesylate and a tosylate. A hydrochloride is more preferred in terms of safety and solubility. One compound of compounds represented by the general formula (1) and/or physiologically acceptable salts thereof may be used alone, or two or more compounds thereof may also be used in combination. The preferred total content of the compounds represented by the general formula (1) and/or physiologically acceptable salts thereof in the pharmaceutical composition for antifungal use of the present invention is preferably 0.01 to 20 w/v % and more preferably 0.1 to 10 w/v % with respect to the total amount of the pharmaceutical composition. The amount of such compounds may be determined on the basis of solubility and formulation property thereof.

<2> Polypropylene Glycol, Diesters of Dibasic Acids, Triacetin, 2-Ethyl-1,3-Hexanediol, Lauromacrogol, and Polyoxyethylene-Polyoxypropylene Glycol to be Incorporated in Pharmaceutical Composition of Present Invention The pharmaceutical composition of the present invention contains, as an essential ingredient, one or more compounds selected from triacetin, polypropylene glycol, diesters of dibasic acids, 2-ethyl-1,3-hexanediol, lauromacrogol, and polyoxyethylene-polyoxypropylene glycol, in addition to the compound represented by the general formula (1) and/or the salt thereof. As for the polypropylene glycol, the polymerization degree thereof is preferably 1000 or more, and more preferably 1500 or more, and the upper limit value of the polymerization degree is preferably 10,000, and more preferably 5000. Preferred examples of dibasic acids constituting the diesters of dibasic acids include tartaric acid, adipic acid, sebacic acid and succinic acid, and adipic acid or sebacic acid is particularly preferred. As the ester moieties thereof, preferred is a hydrocarbon group having 1 to 4 carbon atoms, and specifically, favorable examples of the ester moieties include a methyl ester, an ethyl ester, a propyl ester, an isopropyl ester, a butyl ester, a sec-butyl ester and a tert-butyl ester, and preferred examples thereof include an ethyl ester and an isopropyl ester. Specifically, preferred are diisopropyl adipate and diethyl sebacate. In the pharmaceutical composition of the present invention, the polypropylene glycol, diesters of dibasic acids, triacetin, 2-ethyl-1,3-hexanediol, lauromacrogol, and polyoxyethylene-polyoxypropylene glycol have actions as solvents that stably dissolve the general formula (1), and as inhibitors of the horny cell layer storability of the compounds represented by the general formula (1). In order to exert such actions, each of such ingredients is incorporated at preferably 0.01 to 60 w/v % and more preferably 0.1 to 50 w/v % with respect to the total amount of the pharmaceutical composition. In particular, the content is preferably set up to be a content that can be either decreased or increased. Any of such ingredients also has a subsidiary effect of improving the preservation stability of the compounds represented by the general formula (1) even under a harsh condition of preservation at 60° C. for 1 week.

<3> Glucono-δ-Lactone, Propylene Glycol, Glycerin, and Lactic Acid to be Incorporated in Pharmaceutical Composition of Present Invention The pharmaceutical composition of the present invention is characterized by containing one or more compounds selected from glucono-δ-lactone, propylene glycol, glycerin, and lactic acid, in addition to the compound represented by the general formula (1) and/or the salt thereof. Such ingredients are solvents that stably dissolve the general formula (1) in many cases, and each have an action as an accelerator of the transdermal absorption of the compounds represented by the general formula (1). In order to exert such actions, each of such ingredients is incorporated at preferably 0.01 to 60 w/v % and more preferably 0.1 to 50 w/v % with respect to the total amount of the pharmaceutical composition. In particular, the content is preferably set up to be a content that can be either decreased or increased. Any of such ingredients also has a subsidiary effect for improving the preservation stability of the compounds represented by the general formula (1) even under a harsh condition of preservation at 60° C. for 1 week.

<4> Pharmaceutical Composition of Present Invention

The pharmaceutical composition of the present invention is one for antifungal use, and contains the above-mentioned essential ingredients. Without any particular limitation, the pharmaceutical composition of the present invention can be applied for any formulation with an dosage form known in an antifungal formulation, which formulation can contain the above-mentioned essential ingredients, however, is preferably applied for a skin agent for external use in view of an effect of "capable of controlling the absorbability to the horny cell layer". The pharmaceutical composition of the present invention is preferably formulated into the form of a single-phase solution without containing any flammable solvent such as methyl ethyl ketone, acetone, and ethyl acetate other than ethanol because many of the essential ingredients to be incorporated in the pharmaceutical composition of the present invention have a solvent property or an action of promoting dissolution, superior in an action of inhibiting the absorption and an action of promoting the absorption to the horny cell layer. A cellulose-based thickener such as hydroxypropylcellulose, carboxymethylcellulose, hydroxypropylmethylcellulose, and hydroxyethylcellulose has effects of increasing a viscosity, inhibiting dripping, and enhancing usability, and also has an effect of enhancing the absorbability of a medicament to the horny cell layer. Therefore, in the viscosity adjustment of a system, in some cases, the fine adjustment of the content of such an ingredient causes a variation in horny cell layer storability, so that the maintenance of the bioequivalence becomes difficult. Thus, the bioequivalence can be maintained by applying the pharmaceutical composition of the present invention to a system containing such an ingredient, and adjusting the amount ratio of the above-mentioned two essential ingredients involved in the absorbability to the horny cell layer. Accordingly, it is particularly preferred that the pharmaceutical composition of the present invention be applied for such a dosage form. It should be noted that the term "single-phase solution" as used herein refers to a dissolved liquid substance in which no white turbidity is observed and neither liquid crystal nor microcrystal is observed under a polarized light. In addition, such a viscous solution form can be administered without being spread from a site to be administered even if, for example, being administered to the hair line and the like, and hence is preferably applied as a formulation to be administered to such a site, i.e., in a medicine for antifungal use, a treatment drug for seborrheic dermatitis such as a therapeutic drug for seborrheic dermatitis and a preventive drug for seborrheic dermatitis.

Further, in the above-mentioned composition, the formulation can be performed without incorporating a solvent such as acetone and methyl ethyl ketone other than ethanol because many of the ingredients for promoting the absorption to the horny cell layer and the ingredients for inhibiting the absorption to the horny cell layer as essential ingredients have an excellent solvent effect or an action for promoting dissolution. Therefore, for a treatment drug for seborrheic dermatitis such as a therapeutic drug for seborrheic dermatitis and a preventive drug for seborrheic dermatitis to be administered to a site close to eyes, the probability that a volatile ingredient derived from a solvent irritates eyes is reduced, resulting in an advantageous property.

The pharmaceutical composition of the present invention may contain, apart from the above ingredients, an arbitrary ingredient generally used for formulation. Favorable examples of such an arbitrary ingredient include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, Japan wax, hydrogenated castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, cetyl lactate, diisostearyl malate, ethylene glycol di-2-ethyl hexanoate, neopentyl glycol dicaprate, glyceryl di-2-heptyl undecanoate, glyceryl tri-2-ethylhexanoate, trimethylolpropane tri-2-ethylhexanoate, trimethylolpropane triisostearate, and pentaerythrityl tetra-2-ethylhexanoate; chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexanesiloxane; oil solutions such as silicone oils including modified polysiloxanes such as amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium lauryl sulfate, and triethanolamine alkylether sulfate; cationic surfactants such as stearyl trimethyl ammonium chloride, benzalkonium chloride, and laurylamine oxide; amphoteric surfactants such as imidazoline-based amphoteric surfactants (such as a 2-cocoyl-2-imidazoliniumhydroxide-1-carboxyethyloxy-2-sodium salt), betaine-based surfactants (such as alkyl betaine, amide betaine, and sulfo betaine), and acylmethyl taurine; nonionic surfactants such as sorbitan fatty acid esters (such as sorbitan monostearate and sorbitan sesquioleate), glycerin fatty acids (such as glyceryl monostearate), propyleneglycol fatty acid esters (such as propyleneglycol monostearate), hydrogenated castor oil derivatives, glycerol alkyl ether, POE sorbitan fatty acid esters (such as POE sorbitan monooleate and polyoxyethylene sorbitan monostearate), POE sorbit fatty acid esters (such as POE-sorbit monolaurate), POE glycerol fatty acid esters (such as POE-glyceryl monoisostearate), POE fatty acid esters (such as polyethyleneglycol monooleate and POE distearate), POE alkyl ethers (such as POE2-octyldodecyl ether), POE alkyl phenyl ethers (such as POE nonylphenyl ether), POE/POP alkyl ethers (such as POE/POP2-decyltetradecyl ether), types of tetronic (registered trademark), POE castor oil/hydrogenated castor oil derivatives (such as POE castor oil and POE hydrogenated castor oil), sucrose fatty acid ester, and alkyl glycoside; polyhydric alcohols such as polyethylene glycol, 1,3-butylene glycol, erythritol, sorbitol, xylitol, maltitol, dipropylene glycol, diglycerin, isoprene glycol, 1,2-pentanediol, 2,4-hexanediol, 1,2-hexanediol, and 1,2-octanediol; moisturizing ingredients such as sodium pyrrolidone carboxylate, and sodium lactate; thickeners such as hydroxypropylcellulose, hydroxypropylmethylcellulose, a carboxyvinyl polymer which may be alkyl-modified and/or a salt thereof, carboxymethylcellulose, ethylcellulose, and xanthane gum; pH adjusters such as a buffer salt; and solvents such as benzyl alcohol and ethylene glycol salicylate. Of those ingredients, preferred examples of the ingredients which are preferably contained in the pharmaceutical composition of the present invention include thickeners such as hydroxypropylcellulose, hydroxypropylmethylcellulose, carboxymethylcellulose, ethylcellulose, and xanthane gum. This is because such ingredients act as variation factors of the bioavailability as well as variation factors of physical properties of the formulation, and as a result, the effect of the pharmaceutical composition of the present invention may be thoroughly exhibited. The pharmaceutical composition of the present invention can be produced by treating those ingredients in accordance with a conventional method.

<5> Method for Adjusting Bioequivalence of Pharmaceutical Composition of Present Invention A method for adjusting the bioequivalence of the pharmaceutical composition of the present invention is characterized in that, in terms of the absorbability to the horny cell layer, the pharmaceutical composition is allowed to retain a constant absorption property to the horny cell layer at all times,
by taking a balance of the amount of the ingredient for promoting the absorption selected from glucono-δ-lactone, propylene glycol, glycerin, and lactic acid and the amount of the ingredient for inhibiting the absorption selected from polypropylene glycols, diesters of dibasic acids, triacetin, 2-ethyl-1,3-hexanediol, lauromacrogol, and polyoxyethylene-polyoxypropylene glycol. It should be noted that the phrase "maintaining bioequivalence" as used herein refers to keeping the absorption property of the compounds represented by the general formula (1) to the horny cell layer constant. The content of this ingredient is adjusted in order to adjust the irregularity from lot to lot of the thickener ingredient, and modulate a viscosity. As a result, when the absorbability of a medicament to the horny cell layer is reduced, and thus, the absorbability to the horny cell layer must be increased, there is performed an operation for increasing the total content of the ingredient for promoting the absorption to the horny cell layer with respect to the total amount of the pharmaceutical composition, and/or an operation for decreasing the total content of the ingredient for inhibiting the absorption to the horny cell layer with respect to the total amount of the pharmaceutical composition. The degree of this decrease or increase is preferably calculated and determined from a calibration curve which has been preliminarily drawn on a two-dimensional coordinate by using the mass ratio of the ingredient for promoting the absorption to the horny cell layer and the ingredient for inhibiting transdermal absorption as one axis, and the degree of the absorption to the horny cell layer as the other axis, for example. As a matter of course, such a corrected value may be converted to a mathematical formula by, for example, a multiple regression analysis, and the mathematical formula may also be utilized.

In contrast to the above, when there is a need for decreasing the absorbability to the horny cell layer, there is performed an operation for decreasing the total content of the ingredient for promoting the absorption to the horny cell layer with respect to the total amount of the pharmaceutical composition, and/or an operation for increasing the total content of the ingredient for inhibiting the absorption to the horny cell layer with respect to the total amount the pharmaceutical composition.

As described above, the bioequivalence can be maintained without being affected by the irregularity from lot to lot of a formulation ingredient by adjusting the mixing ratio of the ingredient for promoting the absorption to the horny cell layer and the ingredient for inhibiting the absorption to the horny cell layer.

Hereinafter, the present invention is described in more detail by way of examples. However, it goes without saying that the present invention is not limited to only such examples.

Example 1

Skin agents 1 to 5 for external use, each of which is the pharmaceutical composition of the present invention, were prepared in accordance with the following prescription. That is, luliconazole was dissolved by adding an appropriate amount of ethanol, and to the resulting solution, triacetin and glucono-δ-lactone were added and uniformly dispersed. After that, hydroxypropylcellulose was gradually added, and water was further added to obtain homogenous skin agents for external use. Any of those agents had a viscosity of 100 to 800 mPa·s (viscometer: RE80R manufactured by Toki Sangyo Co., Ltd., and conditions for viscosity measurement: cone angle; 0.8°, cone radius; 2.4 cm, rotation frequency; 10 rpm, and temperature; 25° C.), was not so dripping, and thus was suited as a formulation for seborrheic dermatitis to be administered to the hair line and the like. Further, those agents were free of ingredients strongly exhibiting solvent characteristics like methyl ethyl ketone (MEK) and acetone, did not provide any strong temporary irritation feeling, and could be suitably used for tinea pedis and the like as well.

TABLE 1

| Ingredient | w/v % |
|---|---|
| Luliconazole | 1 |
| Hydroxypropylcellulose | 1.5 |
| Water | 20 |
| Triacetin (TA)* | |
| Glucono-δ-lactone (GL)* | |
| Ethanol | Appropriate amount |
| Total | 100 mL |

*See Table 2

TABLE 2

| Sample | GL (w/v %) | TA (w/v %) | Viscosity (mPa · s) |
|---|---|---|---|
| Skin agent 1 for external use | 3.2 | 0 | 639.6 |
| Skin agent 2 for external use | 3.2 | 12 | 648.8 |
| Skin agent 3 for external use | 1.6 | 12 | 603.0 |
| Skin agent 4 for external use | 1.6 | 24 | 656.6 |
| Skin agent 5 for external use | 0 | 24 | 652.0 |

<Horny Cell Layer Storability Test>

To a plantar part of an isolated guinea pig hind leg, the skin agent for external use was applied at room temperature, and the whole was left out at room temperature for 2 hours. After that, the skin agent for external use was wiped out from the applied site, and further, the applied site was subjected to 5 times of tape stripping with a cellophane tape. Thereafter, the plantar part was excised, and the horny cell layer was peeled off, formed into a piece having a certain size, and evaporated to dryness under reduced pressure for 24 hours. To the obtained dried product, methanol was added, luliconazole as a measurement target was extracted in an ultrasonicator, and filtered through a filter. After that, the concentration of luliconazole in the horny cell layer at two hours after administration was measured with LC-MS/MS (manufactured by Micromass) under the following analysis condition. Table 3 shows the results. The results reveal that any absorption property can be designed by incorporating a combination of the ingredient for inhibiting the absorption to the horny cell layer and the ingredient for promoting the absorption to the horny cell layer, and varying the amount ratio thereof.

<HPLC Condition>

Column: Wakosil II5C18HG, 4.6×250 mm, 5 μm (Wako Pure Chemical Industries, Ltd.)

Mobile phase: 5 mmol/L formic acid aqueous solution: methanol (20:80, v/v)

Flow rate: 1.0 mL/min

Split ratio ca.: 2:8 (MS/MS:drain)

Injection volume: 2 μL

Column temperature: 45° C.

Sample temperature: 5° C.

<MS/MS Condition>

Ionization method: ESI, positive ion mode

Compound: MS1 (m/z), MS2 (m/z)

Measurement ion: luliconazole 354 150

TABLE 3

| Sample | Concentration of luliconazole in horny cell layer (μg/cm$^2$) |
|---|---|
| Skin agent 1 for external use | 1.591 |
| Skin agent 2 for external use | 0.910 |
| Skin agent 3 for external use | 0.598 |
| Skin agent 4 for external use | 0.295 |
| Skin agent 5 for external use | 0.327 |

<Stability in Preservation Under Harsh Condition>

Each of Skin agents 1 to 5 for external use was evaluated for the time-dependent stability of luliconazole under a harsh preservation condition (60° C., 1 week). The quantitative determination of the S-E isomer which was converted from luliconazole by changing the steric structure thereof was performed by HPLC (LC-20AD manufactured by Shimadzu Corporation, HPLC condition: column; CHIRAL-CEL OD-RH 4.6×150 mm, column temperature; 35° C., mobile phase; a mixed solution of methanol/1.8% potassium hexafluorophosphate aqueous solution (83:17, v/v), flow rate; 0.56 mL/min., and detection; 295 nm). Further, the quantitative determination of Z isomers and other analogous substances was performed by HPLC (Agilent 1100 manufactured by Agilent Technologies, HPLC condition: column; Inertsil ODS-2 4.6×150 mm, column temperature; 40° C., mobile phase; 0.13% sodium 1-undecane-sulfonate mixed solution (water/acetonitrile/acetic acid (100) (54:45:1, v/v/v)), flow rate; 1.0 mL/min., and detection; 295 nm). Tables 4 and 5 show the results. The tables reveal that any sample stably exists. That is, in a system of glucono-δ-lactone, triacetin, and hydroxypropylcellulose/ethanol, it can be said that luliconazole stably exists even in preservation under a harsh condition, irrespective of the amount ratio of glucono-δ-lactone and triacetin.

TABLE 4

Immediately after production (weight %)

| Sample | S-E isomer | Z isomer | Total content of other analogous substances |
|---|---|---|---|
| Skin agent 1 for external use | 0.12 | 0.02 | 0.00 |
| Skin agent 2 for external use | 0.13 | 0.02 | 0.00 |
| Skin agent 3 for external use | 0.13 | 0.02 | 0.00 |
| Skin agent 4 for external use | 0.14 | 0.02 | 0.00 |
| Skin agent 5 for external use | 0.13 | 0.02 | 0.00 |

TABLE 5

After preservation for 1 week (weight %)

| Sample | S-E isomer | Z isomer | Total content of other analogous substances |
|---|---|---|---|
| Skin agent 1 for external use | 0.14 | 0.03 | 0.02 |

TABLE 5-continued

| | After preservation for 1 week (weight %) | | |
|---|---|---|---|
| Sample | S-E isomer | Z isomer | Total content of other analogous substances |
| Skin agent 2 for external use | 0.14 | 0.04 | 0.02 |
| Skin agent 3 for external use | 0.13 | 0.04 | 0.02 |
| Skin agent 4 for external use | 0.14 | 0.03 | 0.00 |
| Skin agent 5 for external use | 0.37 | 0.05 | 0.00 |

Example 2

In the same manner as in Example 1, Skin agent 6 for external use as the pharmaceutical composition of the present invention was prepared in accordance with the following prescription. The concentration of luliconazole in the horny cell layer at 2 hours after the application of the agent was 4.532 µg/cm$^2$, and the concentration in Comparative Example 1 in which propylene glycol in the preparation was replaced by ethanol was 0.221 µg/cm$^2$. The S-E isomer measured by HPLC after harsh preservation (60° C., 1 week) was 1.65% in Skin agent 6 for external use, which was higher compared with 1.45% in Comparative Example 1. Propylene glycol is found to be usable as an ingredient for promoting the absorption to the horny cell layer.

TABLE 6

| Ingredient | w/v % |
|---|---|
| Luliconazole | 1 |
| Propylene glycol | 50 |
| Ethanol | Appropriate amount |
| Total | 100 mL |

Example 3

In the same manner as in Example 1, Skin agent 7 for external use as the pharmaceutical composition of the present invention was prepared in accordance with the following prescription. The concentration of luliconazole in the horny cell layer at 2 hours after the application of the agent was 0.584 µg/cm$^2$, and the concentration in Comparative Example 2 in which 2-ethyl-1,3-hexanediol in the preparation was replaced by ethanol was 0.950 µg/cm$^2$. The S-E isomer measured by HPLC after harsh preservation (60° C., 1 week) was 1.06% in Skin agent 7 for external use, which was higher compared with 0.38% in Comparative Example 2. 2-ethyl-1,3-hexanediol is found to be usable as an ingredient for inhibiting the absorption to the horny cell layer.

TABLE 7

| Ingredient | w/v % |
|---|---|
| Luliconazole | 1 |
| Hydroxypropylcellulose | 1.5 |

TABLE 7-continued

| Ingredient | w/v % |
|---|---|
| Water | 20 |
| 2-ethyl-1,3-hexanediol | 5 |
| Ethanol | Appropriate amount |
| Total | 100 mL |

Example 4

In the same manner as in Example 1, Skin agent 8 for external use as the pharmaceutical composition of the present invention was prepared in accordance with the following prescription. The concentration of luliconazole in the horny cell layer at 2 hours after the application of the agent was 0.736 µg/cm$^2$, and the concentration in Comparative Example 3 in which concentrated glycerin (100% glycerin) in the preparation was replaced by ethanol was 0.345 µg/cm$^2$. The S-E isomer measured by HPLC after harsh preservation (60° C., 1 week) was 0.79% in Skin agent 8 for external use, which was higher compared with 0.47% in Comparative Example 3. Concentrated glycerin is found to be usable as an ingredient for promoting the absorption to the horny cell layer.

TABLE 8

| Ingredient | w/v % |
|---|---|
| Luliconazole | 1 |
| Water | 10 |
| Concentrated glycerin | 32 |
| Ethanol | Appropriate amount |
| Total | 100 mL |

Example 5

In the same manner as in Example 1, Skin agent 9 for external use as the pharmaceutical composition of the present invention was prepared in accordance with the following prescription. The concentration of luliconazole in the horny cell layer at 2 hours after the application of the agent was 2.018 µg/cm$^2$, and the concentration in Comparative Example 1 in which lactic acid in the preparation was replaced by ethanol was 0.221 µg/cm$^2$. The S-E isomer measured by HPLC after harsh preservation (60° C., 1 week) was 0.14% in Skin agent 9 for external use, which was lower compared with 1.45% in Comparative Example 1. Lactic acid is found to be usable as an ingredient for promoting the absorption to the horny cell layer.

TABLE 9

| Ingredient | w/v % |
|---|---|
| Luliconazole | 1 |
| Lactic acid | 8 |
| Ethanol | Appropriate amount |
| Total | 100 mL |

Example 6

In the same manner as in Example 1, Skin agent 10 for external use as the pharmaceutical composition of the present invention was prepared in accordance with the following prescription. The concentration of luliconazole in the horny cell layer at 2 hours after the application of the agent was 0.358 μg/cm², and the concentration in Comparative Example 2 in which polyoxyethylene (20)-polyoxypropylene (20) glycol in the preparation was replaced by ethanol was 0.950 μg/cm². The S-E isomer measured by HPLC after harsh preservation (60° C., 1 week) was 1.26% in Skin agent 10 for external use, which was higher compared with 0.38% in Comparative Example 2.

Polyoxyethylene (20)-polyoxypropylene (20) glycol is found to be usable as an ingredient for inhibiting the absorption to the horny cell layer.

TABLE 10

| Ingredient | w/v % |
|---|---|
| Luliconazole | 1 |
| Hydroxypropylcellulose | 1.5 |
| Water | 20 |
| POE (20) POP (20) glycol | 12 |
| Ethanol | Appropriate amount |
| Total | 100 mL |

Example 7

In the same manner as in Example 1, Skin agent 11 for external use as the pharmaceutical composition of the present invention was prepared in accordance with the following prescription. The concentration of luliconazole in the horny cell layer at 2 hours after the application of the agent was 0.148 μg/cm², and the concentration in Comparative Example 1 in which lauromacrogol in the preparation was replaced by ethanol was 0.221 μg/cm². The S-E isomer measured by HPLC after harsh preservation (60° C., 1 week) was 0.19% in Skin agent 11 for external use, which was lower compared with 1.45% in Comparative Example 1. Lauromacrogol is found to be usable as an ingredient for inhibiting the absorption to the horny cell layer.

TABLE 11

| Ingredient | w/v % |
|---|---|
| Luliconazole | 1 |
| Lauromacrogol | 12 |
| Ethanol | Appropriate amount |
| Total | 100 mL |

Example 8

In the same manner as in Example 1, Skin agent 12 for external use as the pharmaceutical composition of the present invention was prepared in accordance with the following prescription. The concentration of luliconazole in the horny cell layer at 2 hours after the application of the agent was 0.199 μg/cm², and the concentration in Comparative Example 1 in which polypropylene glycol 2000 in the preparation was replaced by ethanol was 0.221 μg/cm². The S-E isomer measured by HPLC after harsh preservation (60° C., 1 week) was 0.78% in Skin agent 12 for external use, which was lower compared with 1.45% in Comparative Example 1. Polypropylene glycol 2000 is found to be usable as an ingredient for inhibiting the absorption to the horny cell layer.

TABLE 12

| Ingredient | w/v % |
|---|---|
| Luliconazole | 1 |
| Polypropylene glycol 2000 | 20 |
| Ethanol | Appropriate amount |
| Total | 100 mL |

Example 9

In the same manner as in Example 1, Skin agent 13 for external use as the pharmaceutical composition of the present invention was prepared in accordance with the following prescription. The concentration of luliconazole in the horny cell layer at 2 hours after the application of the agent was 0.306 μg/cm², and the concentration in Comparative Example 2 in which diethyl sebacate in the preparation was replaced by ethanol was 0.950 μg/cm². The S-E isomer measured by HPLC after harsh preservation (60° C., 1 week) was 0.14% in Skin agent 13 for external use, which was lower compared with 0.38% in Comparative Example 2. Diethyl sebacate is found to be usable as an ingredient for inhibiting the absorption to the horny cell layer.

TABLE 13

| Ingredient | w/v % |
|---|---|
| Luliconazole | 1 |
| Hydroxypropylcellulose | 1.5 |
| Water | 20 |
| Diethyl sebacate | 20 |
| Ethanol | Appropriate amount |
| Total | 100 mL |

INDUSTRIAL APPLICABILITY

The present invention is applicable to a pharmaceutical composition such as a skin agent for external use for seborrheic dermatitis.

What is claimed is:
1. A method for treating mycosis of skin comprising administering transdermally to the skin of a subject in need thereof a composition comprising: 1) a compound selected from the group consisting of compounds represented by the general formula (1) below and physiologically acceptable salts thereof; 2) a compound selected from the group consisting of polypropylene glycol, diesters of dibasic acids, triacetin, 2-ethyl-1,3-hexanediol, lauromacrogol, and polyoxyethylene-polyoxypropylene glycol; 3) a compound selected from the group consisting of glucono-δ-lactone, propylene glycol, glycerin, and lactic acid; and 4) ethanol and/or water,

General formula (1)

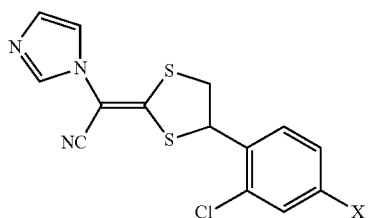

wherein X represents a halogen or hydrogen, wherein the mycosis is seborrheic dermatitis.

2. The method according to claim 1, wherein the compound selected from the group consisting of compounds represented by the general formula (1) and physiologically acceptable salts thereof is luliconazole and/or physiologically acceptable salt thereof

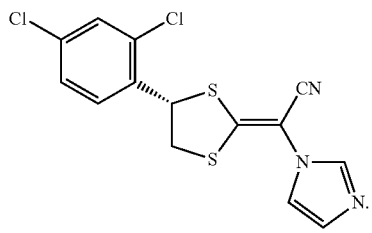

3. The method according to claim 1, wherein the composition comprises triacetin as the compound selected from the group consisting of polypropylene glycol, diesters of dibasic acids, triacetin, 2-ethyl-1,3-hexanediol, lauromacrogol, and polyoxyethylene-polyoxypropylene glycol.

4. The method according to claim 1, wherein the composition comprises glucono-δ-lactone as the compound selected from the group consisting of glucono-δ-lactone, propylene glycol, glycerin, and lactic acid.

5. The method according to claim 1, wherein the composition is in the form of a single-phase solution.

6. The method according to claim 1, wherein the composition comprises glycerin as the compound selected from the group consisting of glucono-δ-lactone, propylene glycol, glycerin, and lactic acid.

* * * * *

UNITED STATES PATENT AND TRADEMARK OFFICE
CERTIFICATE OF CORRECTION

PATENT NO.        : 9,968,591 B2
APPLICATION NO.   : 14/539530
DATED             : May 15, 2018
INVENTOR(S)       : Takaaki Masuda Page 1 of 1

It is certified that error appears in the above-identified patent and that said Letters Patent is hereby corrected as shown below:

In the Specification

In Column 6, Line 46, change "ibota wax," to --ibotta wax,--

In Column 7, Line 17, change "POE sorbit" to --POE sorbitan--

In Column 7, Line 18, change "POE-sorbit" to --POE-sorbitan--

Signed and Sealed this
Twenty-ninth Day of January, 2019

Andrei Iancu
*Director of the United States Patent and Trademark Office*